(12) United States Patent
Lauren

(10) Patent No.: US 7,125,249 B1
(45) Date of Patent: Oct. 24, 2006

(54) ELECTRICALLY POWERED ORTHODONTIC BRACKET AND BONDING METHOD

(75) Inventor: Mark D. Lauren, Amherst, NY (US)

(73) Assignee: Great Lakes Orthodontics, Ltd., Tonawanda, NY (US)

( * ) Notice: Subject to any disclaimer, the term of this patent is extended or adjusted under 35 U.S.C. 154(b) by 176 days.

(21) Appl. No.: 10/762,930

(22) Filed: Jan. 22, 2004

Related U.S. Application Data

(60) Provisional application No. 60/441,497, filed on Jan. 22, 2003.

(51) Int. Cl.
*A61C 3/00* (2006.01)

(52) U.S. Cl. .............................. 433/9; 433/29

(58) Field of Classification Search ............... 433/9
See application file for complete search history.

(56) References Cited

U.S. PATENT DOCUMENTS

| | | | |
|---|---|---|---|
| 5,316,473 A * | 5/1994 | Hare | 433/29 |
| 5,711,665 A * | 1/1998 | Adam et al. | 433/9 |
| 5,791,350 A * | 8/1998 | Morton | 600/590 |
| 6,290,495 B1 * | 9/2001 | Jabri | 433/3 |
| 6,334,772 B1 * | 1/2002 | Taub et al. | 433/24 |
| 6,482,002 B1 * | 11/2002 | Jordan et al. | 433/9 |
| 6,682,344 B1 * | 1/2004 | Stockstill | 433/3 |
| 2003/0190575 A1 * | 10/2003 | Hilliard | 433/6 |
| 2004/0121280 A1 * | 6/2004 | Fischer et al. | 433/29 |

\* cited by examiner

*Primary Examiner*—Ralph A. Lewis
*Assistant Examiner*—Casey Donahoe
(74) *Attorney, Agent, or Firm*—Hodgson Russ LLP

(57) ABSTRACT

An orthodontic bracket design is disclosed together with the associated method of attachment to a tooth wherein the bracket contains an integral light source such as a solid state emitter. The bracket is placed on a tooth using a tool that also provides electrical power to the bracket to cause the integral light emitter to produce radiation of an appropriate wavelength to cure the adhesive used to attach the bracket to a tooth. The electrically powered bracket system overcomes many of the variabilities associated with the current clinical present practice of bonding orthodontic brackets to teeth to provide faster, stronger, and more consistent bonding.

13 Claims, 3 Drawing Sheets

ELECTRICALLY POWERED ORTHODONTIC BRACKET AND BONDING METHOD

CROSS REFERENCE TO A RELATED APPLICATION

Applicant claims priority based on U.S. provisional application No. 60/441,497 filed Jan. 22, 2003 and entitled "Electrically Powered Orthodontic Bracket and Bonding Method", the disclosure of which is incorporated by reference.

BACKGROUND OF THE INVENTION

1. Field of the Invention

This invention broadly relates to methods and apparatus for affixing brackets to the surfaces of teeth as used in orthodontic treatment. More specifically, the invention relates to a novel orthodontic bracket design and the associated bonding methods that provide enhanced clinical convenience and bond strength between the bracket and the tooth.

2. Description of Related Art

Orthodontic treatment involves moving teeth to improve occlusion. Current practice involves cementing slotted orthodontic appliances, known as brackets, to the teeth. To effect movement, an arch wire is inserted into the slot of each bracket. The wire is typically held in the slot by small elastics or wire ligature. The arch wire then exerts appropriate force via the brackets, to move the teeth and effect treatment.

Orthodontic brackets are designed to be bonded directly to the surface of patient's teeth using a bonding adhesive. The adhesives most commonly used are light-curable, and begin to set once light of the appropriate wavelength and intensity is directed onto the adhesive. Light-curable adhesives are generally preferred by orthodontists, as compared to chemically cured adhesives, mainly because the bracket can be readily repositioned prior to fixing it in place using the light.

Current bonding practice involves placing adhesive on the rear face of the bracket base and placing the bracket on a tooth. Some brackets are supplied with preapplied adhesive. The viscous nature of the adhesive causes the bracket to 'stick' to the tooth, allowing it to be repositioned by the orthodontist. A hand-held curing light, typically emitting blue visible light, is then directed along two or more edges of the bracket base to cure the adhesive between the back of the bracket and the tooth. Several practical clinical factors contribute to poor and variable bonding.

Since the curing radiation cannot pass through metal brackets, the adhesive under the bracket base must cure by conducting light from the perimeter of the base through the thin layer of adhesive between the bracket base and the tooth, and by reflecting through the tooth structure. This poor curing mechanism may not sufficiently react the adhesive in the central area of the bracket which can lead to debonding of the bracket when the bracket is subjected to a sufficiently large force.

Other factors contribute to a non-uniform cure of brackets. The orthodontist may typically place all the brackets in a quadrant (about 5) or an entire arch (about 10) prior to curing. In the time from initial placement to actual curing, the bracket may sag slightly or be accidentally touched and moved while placing the other brackets.

To achieve maximum bond strength, the thickness of the adhesive should be kept to a minimum. Pushing the bracket base against the tooth during bonding is the ideal way to both express excess adhesive and ensure intimate contact between the tooth and the bracket. Use of an external curing light prevents the clinician from ensuring intimate contact of the bracket during the curing process.

The intensity of the light that actually impinges on the adhesive depends upon many factors including the distance from the curing light to the bracket edge. While the tip of the light is typically held as closely as possible to the bracket, there is some natural variation in distance. Requiring the light tip to be held closely also poses the risk of touching a bracket, which would move the bracket from its desired position. A significant source of bonding variation is associated with the difficulty accessing all of the edgres of brackets bonded to rear teeth. In addition, variations exist in the type and radiant intensity of commercial curing units, as well as the clinical exposure times used by the orthodontist.

All of these factors affect the quality of cure and bracket adhesion. The clinician wants bracket bonding to be quick, have complete cures, maximum strength, and be consistent. Once the desired location is identified, placement and curing should proceed quickly and consistently.

A variety of approaches have been developed to improve the bonding of orthodontic brackets. Approaches have included new adhesives, priming agents, bracket designs as well as curing lights. Some brackets use bases with undercut regions, roughened surfaces, spherical particles, and fine metal mesh.

One of the more common modifications involves the texture and geometry of the bonding surface of the bracket to enhance the mechanical locking of the adhesive. For example, U.S. Pat. No. 5,267,855 describes the use of partially embedded textured particles on the bonding base and U.S. Pat. No. 5,480,301 teaches the use of a metal mesh, a layer of metallic or plastic particles, grooves and undercuts. U.S. Pat. No. 5,722,826 describes the use of various metal meshes bonded to a photo-etched metal foil backing, as well as sandblasting and even ion bombardment.

One of the earliest proposed design enhancements involves expressing some of the adhesive through the bracket pad to enhance retention. U.S. Pat. Nos. 3,932,940, 4,094,068 and 5,435,720 all describe substantially the same approach, wherein brackets are provided with holes in the base to allow some adhesive to seep through and provide a better lock to the bracket.

Other approaches to improve bracket bonding are based upon variations in the curing light system. Several approaches include the use of light-conducting arch-shaped trays that allow an entire quadrant or arch of positioned brackets to be simultaneously illuminated and bonded. U.S. Pat. Nos. 5,316,473 and 5,813,854 describe such designs which still require an external light source and have the potential for contacting and moving the bracket.

An approach described by Rueggeberg in U.S. Pat. No. 5,800,163, describes a tip to be placed at the end of a curing light assembly. The tip directs the light as a 360° ring towards the edge of the bracket base parallel to the tooth surface. This design is meant to address the problem of accessibility to the bracket edges when bonding to rear teeth, curing all around the perimeter of the bracket pad. The method has the drawbacks of still requiring an external light source and the possibility of physically contacting adjacent brackets by the relatively wide tip design.

Another bracket design approach is found in U.S. Pat. Nos. 5,711,665 and 6,482,002. This orthodontic bracket design allows curing light to be directed normal to the bracket face instead of around the edges. A clear light guide in the body of the bracket is provided that allows curing light to be transmitted through the bracket body and onto the rear bonding surface. This design still requires the use of an external light source, but does begin to address the issue of directing curing light onto the rear bonding face of the bracket instead of the edge.

There is a continuing need to improve the strength, consistency, and efficiency of bonding orthodontic brackets to the patient's teeth to minimize the debonding of brackets during treatment. Premature debonding of orthodontic brackets represents a nuisance to the orthodontist and the patient, since the patient must return to the orthodontist for rebonding or replacement of the detached bracket to resume treatment.

SUMMARY OF THE INVENTION

The invention addresses several of these shortcomings by providing an orthodontic bracket with an integral light source. By electrically exciting the bracket using a hand-held placement tool, the built-in light source is caused to emit light at wavelengths appropriate to curing the adhesive on the rear face of the bracket. Incorporating the light source in the bracket and driving the curing process electrically eliminates nearly all operator variation, the need for an external curing light, the curing time and distance from the bracket, the curing of the central region, and access to brackets bonded to back teeth. The bracket bonding process becomes a well controlled electrically-based process.

Driving the curing process electrically also allows very precise control. A partial cure (or a tack) may be effected to hold the bracket in place to allow removal of exuded adhesive prior to the final cure. Electrical control ensures consistent light intensity and exposure time, eliminating the possibility of undercuring. The light intensity at the back of the bracket is thereby fixed and not dependent upon any operator variables.

More specifically, the invention in one aspect concerns the combination of an orthodontic bracket and a solid state light source assembly. Another aspect of the invention is the associated method of use for the electrically excited bracket.

The method of this invention allows the use of a single tool for placing and curing the bracket on the tooth. The tool design may be slim since it is only mechanical and electrical, and does not require the presence of a fiber optic cable. A slim battery operated tool replaces the currently used placement tool and separate curing light.

Use of the tool also prevents accidental repositioning of the bracket during curing, and provides means for ensuring uniform curing. The tool also allows the orthodontist to press the bracket against the tooth during curing. Exerting a controlled force on the bracket against the tooth during curing ensures a consistently thin layer of adhesive between the tooth and bracket.

The tool can also incorporate a force indicator to assist the orthodontist with applying a consistent force on the bracket against the tooth. The activating tool allows a controlled normal force to be applied to the bracket prior to and during curing. This produces a uniformly thin layer of adhesive. The tool can also incorporate a means for indicating a desired application force—or the attainment of a minimum force.

A further aspect of the invention includes a method of bonding an electrically activated orthodontic bracket to a tooth. The method comprises the general steps of:

1. Providing an orthodontic bracket having an integral light source;
2. Placing an amount of light cure adhesive on the rear bonding surface;
3. Placing the orthodontic bracket on a surface of the tooth using a tool; and
4. Electrically exciting the bracket to affix the bracket to the tooth;

Taken together, the primary elements of this invention:
provide a significant reduction in chairside time for bonding,
eliminate the possibility of displacing brackets from their desired position during curing,
eliminate the access problem to brackets on rear teeth, and
provide consistent and complete curing of the bracket adhesive.

DETAILED DESCRIPTION OF THE PREFERRED EMBODIMENTS

Figure 1:
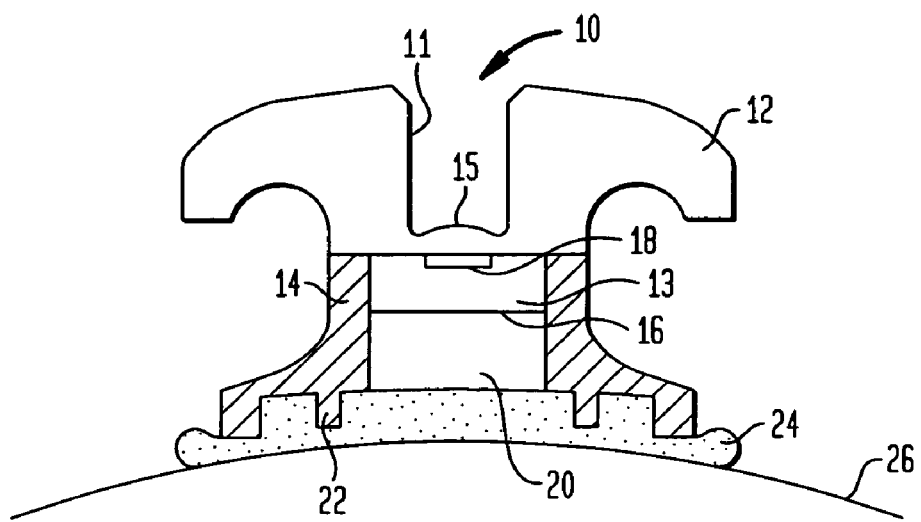
FIG. 1 is an elevational view, partly in section, of an electrically powered orthodontic bracket according to the invention.

The electric bracket of this invention is designated 10 in FIG. 1. A typical arch wire slot 11 is shown as well as a standard tie wing 12. The body of a light module 13 is shown as well as one of its electrical connections 18. The top surface of the electrical connection 18 is below the bottom 15 of the arch wire slot 11, to avoid the arch wire from contacting the top of the light module.

The light emitting face 16 of the module 13 faces the bottom of the bracket. The metal body and base of the bracket 10 has a central opening 20 located between the light emitting face 16 of the module 13 and the base 22 of the bracket. This space may be open or filled with a clear material for conducting the curing light to the rear of the bracket. Alternatively, the light emitting surface 16 may be adjacent to the rear bonding surface 22, in which case the bonding adhesive 24 will directly contact the light emitting surface 16, the body of the bracket, and the tooth surface 26.

Figure 2:
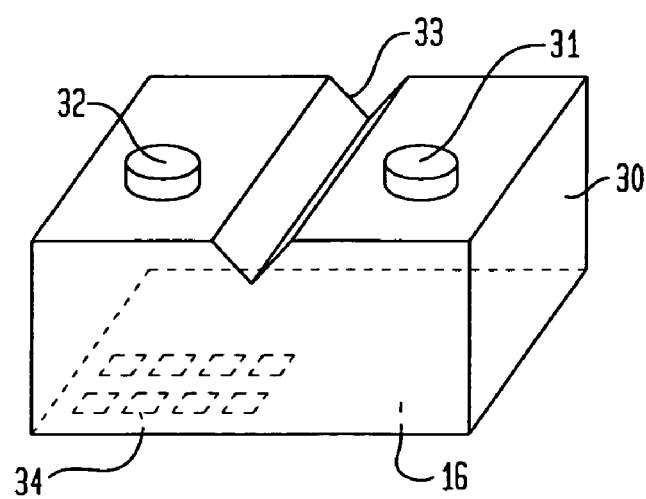
FIG. 2 is a perspective view of an electrically powered light module incorporated in the orthodontic bracket of the invention.

FIG. 2 shows the insulated molded body of a generic light module 30. The module emits curing radiation when electrically powered. Two electrical connections 31 and 32 are formed as surface pads on the module for making contact with a curing and postioning activating tool. A central alignment slot 33 is illustrated that mates with a complimentary shape on the placement tool for orienting the two electrical connections of the tool with the module. Slot 33 preferably is v-shaped but other suitable shapes can be employed. The bottom face 16 of the module consists of an array of small solid state light emitters 34 electrically ganged together and connected to pads 31 and 32.

Figure 3:
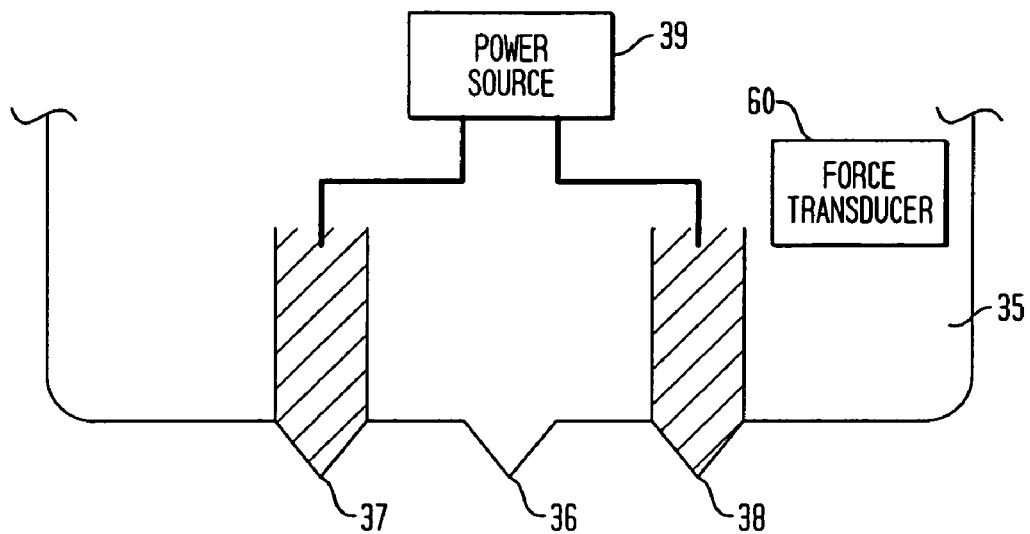
FIG. 3 is a diagrammatic view illustrating the tip of a positioning and activating tool for use with the electrically powered orthodontic bracket of the invention.

FIG. 3 illustrates an example of the tip at one end of the positioning tool. Tool preferably is elongated with the tip shown in FIG. 3 being at one end and a hand grip portion at or near the opposite end. A longitudinal v-shaped extension 36 is designed to fit into groove 33 (FIG. 2) to orient the tool mesial-distally with respect to the bracket. Occlusal-gingival orientation is assured by having the body of the tip engage the arch wire slot (11—FIG. 1). With extension 36 in groove 33, and the body of the tip in the slot, electrical connections 37 and 38 will align and make contact with pads 31 and 32 on the top of the light module. Thus an electrical power source 39, such as a battery, located in the body of tool 35 and connected to terminals 37, 38 is placed in a circuit with the light emitters 34 to energize the same.

Figure 4:
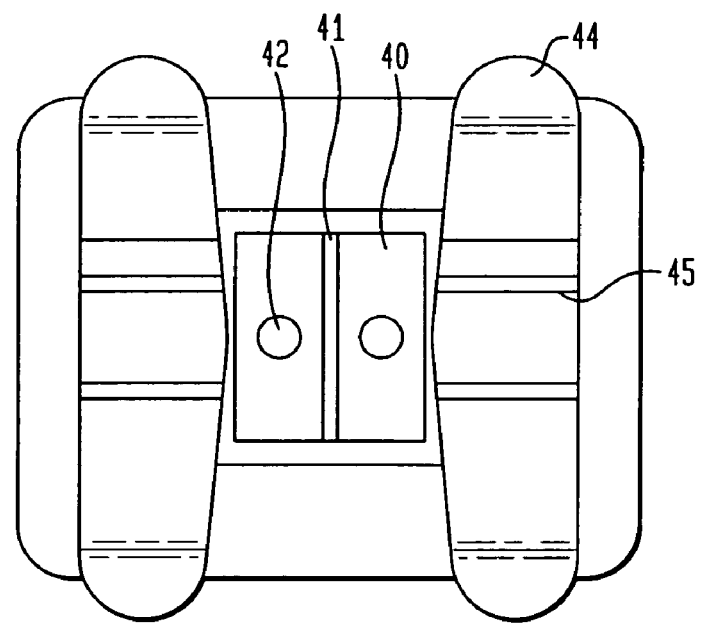
FIG. 4 is a plan view of the electrically powered orthodontic bracket of the invention.

FIG. 4 is a top view of a bracket showing the location of the light module 40 between the tie wings 44. The tool alignment groove 41 lies between the two electrical contact pads 42, which are aligned with the center of the arch wire slot 45.

Figure 5:
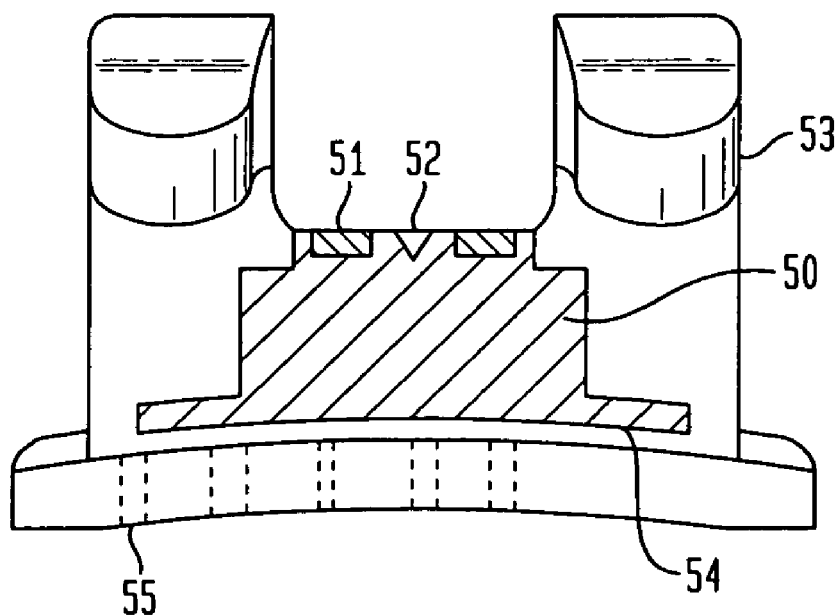
FIG. 5 is an elevational view, partly in section, of the electrically powered orthodontic bracket of the invention.

FIG. 5 shows a side view of an electrically powered bracket according to the invention showing an integral light module 50, top electrical connections 51 and alignment groove 52 which lie below the level of the arch wire slot 53. In this embodiment, the light emitting surface 54 of the light module 50 is extended down towards the base which is perforated with channels 55 to accommodate adhesive, light penetration, and mechanical interlocking for bracket retention.

In the bracket shown in FIGS. 1, 4 and 5 of the integral light module 13, 30, 40, 50 may be mounted in the base or the body of the bracket. Means are provided to conduct the emitted light to the rear face of the bracket, using for example: fiber optics, optically clear materials, or optically reflective materials. Alternatively, the emitting surface may be directly bonded to the tooth. A light conducting lining on the rear face of the bracket may also be used, or such as short lengths of optical fiber fused to the rear surface or glass beads fused to the rear face.

The integral light source 13, 30, 40, 50 may consist of a solid state light emitter such as a light emitting diode, surface mount LED, micro LED, laser diode, microchip laser, or an electroluminescent device. One example may be blue CyberLites from Kopin Corporation (Taunton, Mass.) which are made using nanotechnology and are smaller than a grain of sand. An array of miniature devices, such as those designated 34 in FIG. 2, built with a specifically shaped light emitting surface may be used to irradiate the rear face of a bracket.

The array is driven using electrical connections at the top surface of the bracket which allow the tool 35 of FIG. 3 to connect with the bracket. The tool 35 can directly contact and make electrical connection with the top surface of the light module. In this case, the module would be constructed to have its electrical connections on the rear face, in the form of two metal pads. Between the pads would be molded insulating material of the body of the module.

Alternatively, the tool 35 would electrically connect to the module through part of the metal bracket. In this case, the electrical connections to light module are brought to the top face of the bracket via insulated channels. The electrically conducting center of an insulated channel may be used to connect with the placement tool.

Appropriate grounding procedures and effects must be considered to safely applying a floating DC voltage (from a battery-driven tool) directly to a patient. The body of a metal bracket may serve as a useful ground.

The orthodontic bracket of this invention requires a complementary-designed tool, i.e. the tool 35 of FIG. 3. This tool is designed to pick-up, place, and cure the bracket to the tooth. The tool has a source 39 of electrical power suitable to drive the light module in the bracket. Pushing the tool against the bracket ensures proper electrical contact between the tool end the bracket. This also expresses extra material to minimize the thickness of the adhesive.

The slim hand-held tool is designed to physically engage the arch wire slot and electrically connect to the bracket. The tool may also include means for locating and aligning the bracket with respect to the tooth. Two electrical connections must be made to supply power to the light system. The tool may contain a rechargeable battery operated, disposable Tool tips may be disposable, or reused and autoclavable.

Electrically controlling the brightness of the curing light provides almost direct control over the chemistry. Curing times and intensities could be optimized for specific adhesives by the manufacturer. Light modules could also be designed for specific adhesives. Cures could be easily ramped and digitally controlled directly on the tool.

As an electrical device, the tool could also include various devices and transducers. The tool may have means in the form of force transducer 60 for measuring and indicating the force used to press the bracket against the tooth. A display could indicate a desired force level or range. The curing signal could also be interlocked to only allow curing beyond a certain applied force. The bracket placement/curing tool may be hand-held or part of an automated or computer controlled placement system.

The basic design principles of this invention may be duplicated by a variety of manufacturing methods. Currently these methods include computer-driven machine centers, lasers, and water jets. Digitally-based manufacturing using rapid prototyping methods is also known, for example stereo lithography, laser sintering and laser engineered net shaping.

While embodiments of the invention have been described in detail, that is for the purpose of illustration, not limitation.

The invention claimed is:

1. An orthodontic bracket comprising:
   a base with an outer surface provided with light curable adhesive for bonding to a tooth surface,
   a body extending from the base which contains a slot for an arch wire, and tie wing means for securing an arch wire into the slot, and
   an integral light emitting element that, when electrically excited, emits radiation to cure the adhesive and effect bonding, the light emitting element being built-in the body so as to be fixed therein.

2. The bracket of claim 1 wherein the light emitting element consists of a light emitting diode, diode chips, semiconductor dies, semiconductors capable of radiative recombination of electron-hole pairs, or electroluminescent elements, as individual elements or assembled into arrays or bundles.

3. A kit comprising the combination of an orthodontic bracket and a placement tool wherein the orthodontic bracket comprises:
   a base with an outer surface provided with light curable adhesive for bonding to a tooth surface,
   a body extending from the base which contains a typical arch wire slot and tie wings, and
   an integral light emitting element that, when electrically excited, emits radiation suitable for curing the adhesive, the light emitting element being built-in the body so as to be fixed therein; and wherein
   the placement tool has a body including means to mechanically and electrically engage the bracket for the purpose of placing the bracket on the tooth and electrically exciting the integral light emitting element.

4. The kit of claim 3 wherein the tool is provided with means to provide an indication of the normal force applied to the bracket during bonding.

5. The kit of claim 3 where the tool has an adjustable angle to accommodate placement of brackets on back teeth.

6. The kit of claim 3 wherein the tool has a mirror or electronic video capability to assist with bracket placement.

7. A method of attaching an orthodontic bracket to a tooth comprising:
   a) providing an orthodontic bracket having an integral electrically generated light source built-in the bracket so as to be fixed therein;
   b) placing an amount of light curable adhesive on a rear bonding surface of the bracket;
   c) placing the orthodontic bracket on a surface of the tooth using a tool; and
   d) electrically exciting the light source in the bracket to cure the adhesive and affix the bracket to the tooth.

8. The method of claim 7, wherein the light source is electrically excited by an electrical power source in the tool.

9. A tool for grasping, locating, and curing an adhesive-bearing orthodontic bracket, said tool providing electrical power to the bracket to illuminate an internal light source and effect curing of the adhesive to secure the bracket to a tooth, the light source being built-in the bracket so as to be fixed therein.

10. The orthodontic bracket according to claim 9 wherein the body includes means for effecting electrical connection between the light source and an external electrical power source.

11. A method according to claim 10, wherein the light source is energized in response to generation of means external to the bracket.

12. An electrically powered and optically enhanced orthodontic bracket comprising:
   a) a body having a surface provided with optically curable adhesive thereon for securing the bracket to a tooth;
   b) an electrically operated light source built-in and fixed within the body which when electrically energized emits radiation to cure the adhesive and effect bonding of the bracket to a tooth; and
   c) an optical path extending from the light source through the body for conducting light to the adhesive for curing the same to secure the bracket to a tooth.

13. A method for securing an orthodontic bracket to a tooth comprising:
   a) providing an orthodontic bracket having light curable adhesive on a surface thereof, an integral electrically operated light source and a light conducting path from the light source through the bracket to said surface, the light source being built-in the bracket so as to be fixed therein;
   b) positioning the bracket so that the adhesive contacts a surface of the teeth; and
   c) energizing the light source to transmit light through the light conducting path in the bracket to cure the adhesive and secure the bracket to the tooth.

* * * * *